United States Patent [19]

Hegde et al.

[11] Patent Number: 4,788,211

[45] Date of Patent: Nov. 29, 1988

[54] ANTIFUNGAL COMPOUND AND AFC COMPLEX PRODUCED FROM ACTINOMADURA SCC 1838

[75] Inventors: Vinod R. Hegde, Rockaway; Mahesh G. Patel, Verona; Ann C. Horan, Summit; Ingrid-Agneta Gunnarsson, Hackettstown, all of N.J.

[73] Assignee: Schering Corporation, Kenilworth, N.J.

[21] Appl. No.: 89,297

[22] Filed: Aug. 25, 1987

[51] Int. Cl.[4] .................. A61K 31/415; C07D 233/02
[52] U.S. Cl. .................... 514/392; 548/315; 435/253
[58] Field of Search .................. 548/315; 514/392

[56] References Cited

U.S. PATENT DOCUMENTS 4,686,231 8/1987 Bender et al. ............... 548/315

Primary Examiner—Mary C. Lee
Assistant Examiner—J. Richter

Attorney, Agent, or Firm—Thomas D. Hoffman; Stephen I. Miller; James R. Nelson

[57] ABSTRACT

The invention relates to an antifungal compound of the following structural formula

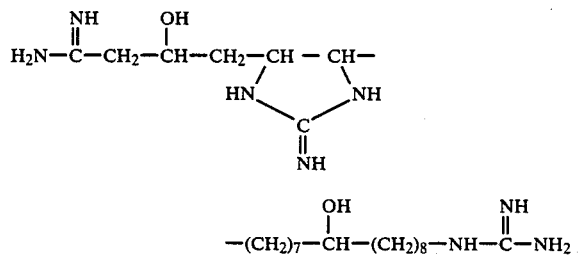

which is isolated from the AFC complex elaborated by the microorganism Actinomadura sp: nov SCC 1838, ATCC 53656.

5 Claims, No Drawings

ANTIFUNGAL COMPOUND AND AFC COMPLEX PRODUCED FROM ACTINOMADURA SCC 1838

BACKGROUND OF THE INVENTION

This invention relates to a new antifungal compound containing a cyclic guanido group and two terminal quanido groups. The compound is isolated from an antifungal complex designated AFC, which complex is produced in fermentation under controlled conditions using a biologically pure culture of the microorganism, Actinomadura sp. SCC 1838, ATCC 53656.

SUMMARY OF THE INVENTION

The present invention embraces Actinomadura sp. SCC 1838, ATCC 53656 and mutants and variants thereof having the identifying characteristics of Actinomadura sp. SCC 1838, ATCC 53656.

Another aspect of the present invention is directed to the AFC complex produced by cultivating a strain of Actinomadura sp. SCC 1838 having the identifying characteristics of ATCC 53656 in a pH and temperature controlled aqueous nutrient medium having assimilable sources of carbon and nitrogen under controlled submerged aerobic conditions until a composition of matter having substantial antifungal/antibiotic activity is produced.

The present invention is also directed to a component of the AFC complex, i.e. a compound represented by the formula:

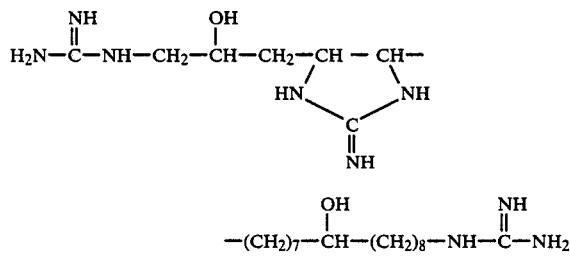

in racemic or optically active form, or a pharmaceutically acceptable salt thereof.

FERMENTATION OF THE MICROORGANISM

The AFC complex of this invention is produced when the elaborating microorganism, Actinomadura sp. SCC 1838 is grown in an aqueous nutrient medium under submerged aerobic conditions at a temperature of about 27° C. to 40° C., preferably at from 27° C. to 35° C., and at a pH of from about 6.5 to 8.0 with agitation until substantial antibiotic activity is imparted to the medium. Temperature studies indicate that the organism grows rapidly at about 30° C. Therefore, the fermentation is preferably conducted employing a single temperature pattern of 30° C. for a period of about 24 to 96 hours. The fermentation is generally conducted from about 3 to 7 days, preferably for about 3 days. To determine when peak antibiotic production has been reached, samples of the medium are assayed every 24 hours for antibiotic content by bioassay of the whole broth against Candida albicans Wisconsin. The growth of the organism (packed cell volume), pH and dissolved oxygen levels were determined either intermittantly or continuously.

As nutrient medium, there is employed any suitable medium containing a source of carbon, for example an assimilable carbohydrate, and a source of nitrogen, for example an assimilable nitrogenous or proteinaceous material.

The medium employed for the fermentation contains casamino acids and cornstarch as the major sources of nitrogen and carbon, respectively. Under these conditions, the microorganism produces the AFC complex of this invention containing at least 3 biologically active components as determined by bioautography against both C. albicans Wisconsin of the complex after development of a thin layer chromatography plate in 2:2:1 (v/v/v) chlorofrom: methanol: pH 3.5 acetate buffer.

The foregoing media are exemplary of the nutrients utilized by Actinomadura sp. SCC 1838 to produce the antifungal/antibiotic AFC complex of this invention. However, it is obvious to those skilled in the fermentation art that a wide range of nutrients obtained from a number of suppliers may be substituted for the foregoing, and that generally good growth and antibiotic production can be obtained, such nutrients bein the functional equivalent to those set forth herein.

The fermentation is generally conducted by initially sterilizing the fermentation medium prior to the addition of the inoculum.

The pH of the fermentation medium is generally maintained at from about 6.5 to 8.0, a pH of from about 6.5 to 7.5 being preferred. Prior to sterilization, the pH of the medium is usually adjusted to about 7.5 and prior to inoculation the pH is usually about 6.7.

The fermentation was initiated by the addition of the inoculum to the sterilized fermentation medium. Generally, inoculum volume is 5% of total medium volume. The inoculum is prepared by addition of a sample of the frozen whole broth to an appropriate germination medium. A particularly preferred germination medium comprises 0.3% (w/v) of beef extract, tryptone, 0.5%; yeast extract, 0.5%; cerelose, 0.1%; potato starch, 2.4%; $CaCO_3$, 0.2%. The pH medium of the germination medium is not adjusted. There are usually two inoculum stages each lasting for 2 days a 30° C.

The fermentation medium is made up of 0.1% (v/v) of 0.14 g Fe (II) $SO_4$/liter, beef extract, 0.25% (w/v); casamino acids, 0.1%; maltose, 0.25%; cerelose 0.25%; corn starch, 2%; yeast extract, 0.2%; and 3-[N-Morpholino]propanesulfonic acid [MOPS] 1%. The pH o fermentation medium is adjusted to 7.5 prior to addition of MOPS and sterilization. The fermentation stage usually requires from 24 to 120 hours with 3 days preferred and is generally conducted at about 30° C.

ISOLATION AND PURIFICATION OF AFC COMPLEX AND THE COMPOUND OF THIS INVENTION

The AFC complex of this invention is produced when the elaborating organism, Actinomadura sp. SCC 1838 having the identifying characteristics of ATCC 53656 is grown in the appropriate nutrient medium.

The AFC complex of this invention contains at least three (one major and two minor components) biologically active components. Initial isolation studies show that these three components are polar, cationic and water soluble compounds and not extractable with solvents. Accordingly, the AFC complex containing the three components is separated from the fermentation broth by filtration, absorption on a polystyrene resin, followed by elution of the resin with acidic methanol to give a AFC complex as a solid.

The compound of this invention is the major component of AFC complex and is isolated therefrom by absorption of the AFC complex on a cation exchange chromatography using, for example, a CM Sephadex C-25 (Na+) column, followed by elution with aqueous NaCl gradient. Reverse phase chromatography of the eluant on for example, a Whatman LRP-2 (C-18) column eluting with a methanol/water gradient gives an active fraction from which the compound of this invention is isolated.

Using the above procedure, 101.6 mg of the compound of the invention was obtained from 100 L of fermentation broth. The physicochemical data for the compound of this invention is given in Table I

TABLE I

| | |
|---|---|
| $[\alpha]_D^{26}$ | −1.5 (MeOH, c 0.5) |
| IR(KBr) $\gamma$max cm$^{-1}$ | 3430, 2930, 2850, 1670, 1650, 1460, 1140, 1110, 620 |
| UV $\lambda$max(MeOH) nm | End absorption |
| FAB Mas Spec. | 498(M + 1) |
| High Res. Mass | Calc for $C_{24}H_{52}N_9O_2$ 498.4240 Found 498.4239 |
| $^1$H NMR (D$_2$O) | 4.1(m,1H), 3.95(m,1H), 3.8(m,1H), 3.5(m,1H), 3.25(dd,1H), 3.1(dd,1H), 3.05(t,2H) 2.5(m,1H), 2.3(m,1H), 2.2–1.4 (several CH$_2$) |
| $^{13}$C NMR (D$_2$O) | 27.05, 27.07, 27.76, 28.22, 30.28, 30.67, 30.81, 30.87, 30.91, 30.95, 31.08, 31.11, 34.95, 38.21, 38.26, 43.64, 49.75, 56.93, 60.90, 68.89, 74.07, 159.07, 159.72, 161.38 |
| $^{15}$N NMR (D$_2$O) | 142.94(1N), 146.22(4N), 155.83(1N), 161.88(1N), 169.86(2N) |

TAXONOMY OF ACTINOMADURA sp. SCC 1838, ATOC 53656

Actinomadura sp. SCC 1838, ATCC 53656 was isolated from a Florida soil sample by plating soil dilutions on minimal media containing 5 mcg/mL of neomycin.

Cultural Characteristics of Actinomadura sp. SCC 1838 ATCC 53656

Actinomadura sp. forms abundant yellowish pink to pink aerial mycelia. The color of the colony reverse violet red.

Morphological Characteristics of Actinomadura sp. SCC 1838 ATCC 53656

The organism is filamentous with a well-developed substrate.

*Aerial mycelia* bear chains of spores that appear as tight hooks and pseudosporangia.

Cell Chemistry: Whole cells of Actinomadura sp. ATCC 53656 contain meso-diaminopimelic acid and madurose.

Generic Identification. Based on the morphology and cell chemistry, SCC 1838, ATCC 53656 is identified as a species of Actinomadura.

THE MICROORGANISM

The microorganism used according to the present invention for the production of the AFC complex of the invention is Actinomadura sp. SCC 1838.

A viable culture of this microorganism has been deposited in the collection of the American Type Culture Collection (ATCC) in Rockville, Md., where it has been assigned accession number ATCC 53656. Should the deposited culture become lost, destroyed or non-viable during the longer of the thirty (30) year period from the date the culture was deposited or the five (5) year period after the last request for the deposited culture or the effective life of the patent which issues from this application the culture will be replaced upon notice by applicants or assignee(s) of this application. Subcultures of Actinomadura sp. SCC 1838, ATCC 53656 are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the U.S. Patent Laws.

BIOLOGICAL ACTIVITY OF AFC COMPLEX AND THE COMPOUND OF THIS INVENTION

The HPHG complex exhibits both antifungal and antibacterial activity in vitro against Gram positive and Gram negative microorganisms.

The compound of this invention isolated from AFC complex exhibits very good in vitro antifungal activity against seven species of Candida and six species of dermatophytes and slight activity against an intravaginal Candida infection in hamsters. The in vitro antifungal results are summarized in Table II and provide the geometric mean MIC (mcg/mL).

TABLE II

| | Antifungal Activity (MIC, mcg/ml) | | |
|---|---|---|---|
| | MEDIA | | |
| Microorganism | SDB[1] | EMEM[2] | MA[3] |
| Candida (seven species) | ≧58 | <0.03 | ≦1.4 |
| Dermatophytes (six species) | ≦0.13 | — | 2.5 |

[1]Sabouraud dextrose broth medium
[2]Eagles Minimum Essential Medium
[3]MA Medium - (Milewski, S., et al. 1983, Arch. Microbiol., 135: pp. 130–136)

The iv LD$_{50}$ for the compound of this invention in mice was about 1.5 mg/kg.

PHARMACEUTICAL COMPOSITION

This invention also contemplates antifungally effective pharmaceutical compositions comprising an antifungally effective amount of a compound of formula I or its pharmaceutically acceptable salts in admixture with a pharmaceutically acceptable, non-toxic carrier adapted for topical, oral or parenteral use.

Topical dosage forms may be prepared according to procedures well known in the art, and may contain a variety of ingredients. The formulations for topical use include ointments, creams, lotions, powders, aerosols, vaginal tablets, pessaries and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcuim phosphate, or boric acid. Aqueous suspensions of the above powders may also be made. Solutions or emulsions may also be prepared using inert solvents which are preferably nonflammable, odorless, colorless and nontoxic, for example vegetable oils, isopropanol, dimethyl sulfoxide, hydrogenated naphthalenes, and alkylated naphthalenes. Similarly, aerosol or non-aerosol sprays may be prepared using solutions or suspensions in appropriate solvents, e.g., difluorodichloromethane for aerosols.

In the case of topical formulations, e.g., ointments, creams, lotions, powders, tablets, pessaries or sprays, the formulation will contain about 0.1 to 10 grams of a compound of formula I per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and may contain salts or glucose to make the solution isotonic.

In general, the dosage of compounds of formula I administered to combat a given fungal infection is similar to the dosage requirements of the present commerical products miconazole, clotrimazole, and ketoconazole.

In general, the topical dosage range is from about 0.1% to about 10% by weight of a particular pharmaceutical composition formulated in single or divided doses, with the preferred range being about 0.5% to about 4% and with the most preferred range being about 1% to about 2%.

It will be appreciated that the actual preferred dosages of the compounds of this invention or pharmaceutically acceptable salts thereof will vary according to the particular compound being used, the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

The following examples illustrate the invention:

EXAMPLE 1

Preparation of the AFC Complex

A 100 liter batch containing AFC Complex was prepared as follows:

A. Inoculum Preparation

The first seed stage was inoculated with 2.5 mL of frozen whole broth into sixteen 250 mL Erlenmeyer flasks, each containing 50 mL of a medium consisting of beef extract, 0.3% (w/v); tryptone, 0.5%; yeast extract, 0.5%; cerelose, 0.1%; potato starch, 2.4%; and $CaCO_3$ 0.2%. This first stage was shaken at 30° C. on a 2" stroke rotary shaker at 300 rpm for 48 hrs. A second germination stage was prepared by inoculating twenty-three 2000 mL Erlenmeyer flasks each containing 350 mL of above medium with 25 mL of the first stage inoculum. This second stage was incubated at 30° C., shaking on a 2" stroke rotary shaker at 300 rpm, for 48 hrs.

B. Fermentation

These flasks from the second stage were pooled and inculated into a 140 liter in-place-sterilizable fermentation vessel (NBS fermentor) containing 100 liter of a fermentation medium containing 0.014g of Fe (II) $SO_4$/liter, beef extract, 0.25%; casamino acids, 0.5%; corn starch, 2%; yeast extract, 0.2%; and 3-[N-Morpholino]-propanesulfonic acid [MOPS] 1%. A sterile water solution containing 250 g of cerelose and 250 g of maltose was added to the vessel at this time. The starting pH after inoculation was 6.7. The fermentation was run at 30° C., 1.8 cubic feet of air/min. and 350 rpm for 72 hrs. The final pH was 7.5, packed cell volume 1.4 and sugar $\frac{1}{2}$%.

EXAMPLE 2

Isolation and Separation of AFC Complex

A. Isolation

The whole broth from a 100 liter fermentation of Example 1 was filtered and the clarified filtrate was absorbed to XAD-16 in a column, 30"×2.5". The XAD-16 was washed with water and then methanol. The antifungal complex (AFC) was eluted with four liters of acidic methanol (nominal pH 2.0). The methanol was evaporated to yield 12.2g of the AFC which was dissolved in 100 ml of water and loaded onto CM Sephadex C-25 ($Na^+$) in a column, 7"×2.5". The column was washed with 4 liters of water and then eluted with 3 liters of 0.5N and 1.0N NaCl. The antifungal active fractions were combined and loaded on reverse phase LRP-2 resin in a 5.5"×2.5" column. The resin was washed with 5 liters of water and eluted with 50% aqueous methanol. The methanol was evaporated and the residual water was removed by lyophilization to yield 101.6 mg of pure compound of this invention. The physicochemical data for the compound of this invention is given in Table I.

What is claimed is:

1. The compound represented by the formula

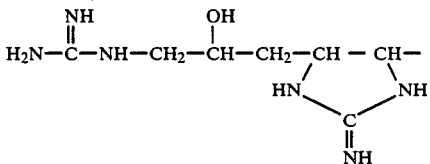

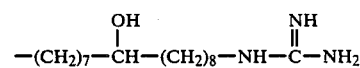

in racemic or optically active form, or a pharmaceutically acceptable salt thereof.

2. An antifungal composition comprising a pharmaceutically acceptable carrier and an antifungally effective amount of AFC complex or the compound of claim 1.

3. An antifungal composition of claim 2 which comprises the AFC complex.

4. An antifungal composition of claim 2 which comprises the compound.

5. AFC complex produced by cultivating a strain of Actinomadura sp. SCC 1838 having the identifying characteristics of ATCC 53656 in a pH and temperature-controlled aqueous nutrient medium having assimilable sources of carbon and nitrogen under controlled aerobic conditions until a composition of matter having substantial antifungal activity is produced.

* * * * *